United States Patent [19]
Williams et al.

[11] Patent Number: 6,123,828
[45] Date of Patent: Sep. 26, 2000

[54] METHOD AND APPARATUS FOR MEASURING ETHANOL VAPOR CONCENTRATION

[75] Inventors: Paul M. Williams, South Glamorgan; Dylan Jones, Cardiff, both of United Kingdom

[73] Assignee: Lion Laboratories Limited, South Glamorgan, United Kingdom

[21] Appl. No.: 09/091,450

[22] PCT Filed: Dec. 12, 1996

[86] PCT No.: PCT/GB96/03064

§ 371 Date: Sep. 17, 1998

§ 102(e) Date: Sep. 17, 1998

[87] PCT Pub. No.: WO97/21999

PCT Pub. Date: Jun. 19, 1997

[30] Foreign Application Priority Data

Dec. 14, 1995 [GB] United Kingdom .................... 9525513

[51] Int. Cl.⁷ .................................................. G01N 27/404

[52] U.S. Cl. ........................... 205/787; 204/415; 204/432; 205/782.5

[58] Field of Search ...................................... 204/415, 431, 204/432; 205/782.5, 783, 787

[56] References Cited

U.S. PATENT DOCUMENTS

| Re. 31,915 | 6/1985 | Oswin et al. ........................... 204/432 |
| 3,342,558 | 9/1967 | Reinecke ................................. 205/787 |
| 4,127,780 | 11/1978 | Kimbell . |

FOREIGN PATENT DOCUMENTS

| 0172969 A2 | 3/1986 | European Pat. Off. . |
| 0607756A2 | 7/1994 | European Pat. Off. . |

*Primary Examiner*—T. Tung
*Attorney, Agent, or Firm*—King and Schickli, PLLC

[57] ABSTRACT

A method and apparatus for measuring ethanol vapor concentration wherein a cell output is plotted with respect to time. The gradient of the steady rate portion of the plot is determined and an ethanol vapor concentration signal is generated from the determined gradient.

9 Claims, 4 Drawing Sheets

METHOD AND APPARATUS FOR MEASURING ETHANOL VAPOR CONCENTRATION

This invention relates to a method of measuring ethanol vapour concentration and is particularly, but not exclusively, directed to the measurement of breath alcohol concentration (BAC).

Fuel cells are extensively used in equipment for detecting and/or measuring ethanol vapour concentrations. As is well known the oxidation of the volatile component in the fuel cell results in a potential difference being developed between a working electrode and a counter electrode, the potential difference being proportional to the concentration of the volatile component. This potential difference can be used to give a quantitative ethanol vapour measurement, either by monitoring the voltage directly or the resulting current, and typical existing methods of developing that measurement utilise either the peak height of the curve or a calculation of the area under the curve. To obtain meaningful results from either the measurement of the peak height or the area under the curve, a fixed volume of sample must be supplied to the fuel cell and hence a sampling system is required. The time taken between the delivery of the sample to the fuel cell to the display of the measurement is typically of the order of 20 to 30 seconds. Sampling systems can make the apparatus quite bulky and expensive, whilst response times quickly mount up when extensive screening programmes are in operation.

From one aspect the invention consists in a method of measuring ethanol vapour concentration comprising:

introducing a sample into a fuel cell to generate an output which is proportional to the vapour concentration, said output rising to a peak at a substantially steady rate after an initial non-linear portion, determining the gradient of the steady rate portion of the output, and generating an ethanol concentration signal from the determined gradient.

Thus the applicants have determined that the gradient of the steady state part of the graph is directly proportional to the vapour concentration and so a reading can be obtained within a very short time (typically under 5 seconds), simply by exposing the fuel cell to the ethanol vapour, i.e. there is no need for a sampling system of the sort previously utilised.

The gradient may be conveniently determined in a predetermined time window after the start of the output. As has been indicated earlier this is less than 5 seconds, but not immediate due to an initial non-linear portion of the output. Additionally or alternatively the method may include comparing successive gradient determinations and selecting a gradient determination for generating the concentration signal after at least a pair of successive determinations are substantially equal. This equality should indicate that the determination is being made in relation to a linear portion of the output.

From a further aspect the invention consists in apparatus for measuring ethanol vapour concentration including:

a fuel cell for generating an output which is proportional to the concentration of the vapour to which it is exposed, said output rising to a peak at a substantially steady rate after an initial non-linear portion, means for determining the gradient of the steady rate portion of the output and, means for generating an ethanol vapour concentration signal from the determined gradient.

In arrangements such as BAC measurement, it is often desirable to sample a flow of the gas bearing the vapour and it has been found that such fuel cells can be made flowrate insensitive, if a gas permeable membrane or some other structure which prevents flow induced local gas movement, overlies the working electrode. The apparatus therefore includes such a membrane or structure. If a membrane, it may be hyrophobic and, for example, it may be a PTFE membrane.

The apparatus may have a body defining a sample path (e.g. a breath tube) and the apparatus may then further comprise means for exposing the fuel cell to vapour in the sample path.

In one arrangement the fuel cell may lie adjacent to the flow part, but separated there from by a shutter, such as an iris shutter. Alternatively a sample may be drawn to the working electrode of the fuel cell by a change in relative pressure between the vicinity of the fuel cell and the sample part. As no specific volume has to be drawn this could be achieved, for example, by introducing a restriction into the sample path.

Although the invention has been defined above it is to be understood that it includes any inventive combination of the features set out above or in the following description.

BRIEF DESCRIPTION OF THE DRAWINGS

The invention may be performed in various ways and specific embodiments will now be described, by way of example with reference to the accompanying drawings, in which:

FIG. 1 shows diagrammatically the shape of a typical fuel cell output after the cell has been exposed to ethanol vapour concentration. It will be noted that after a first non-linear portion (a), the graph rises substantially linearly (b) until just before a peak (c) is reached. For the purposes of this specification the gradient of portion (b) will be referred to as the 'initial gradient'. Until now a determination of the vapour concentration has been calculated either from the height of the peak (c) or from an area under the graph following the peak (c). An example of such an approach is described in British Patent No. 2201245. As can be seen from that document the time taken before a response can be generated is quite considerable and the accuracy depends on a particular volume of sample being delivered to the fuel cell.

Figure 1:
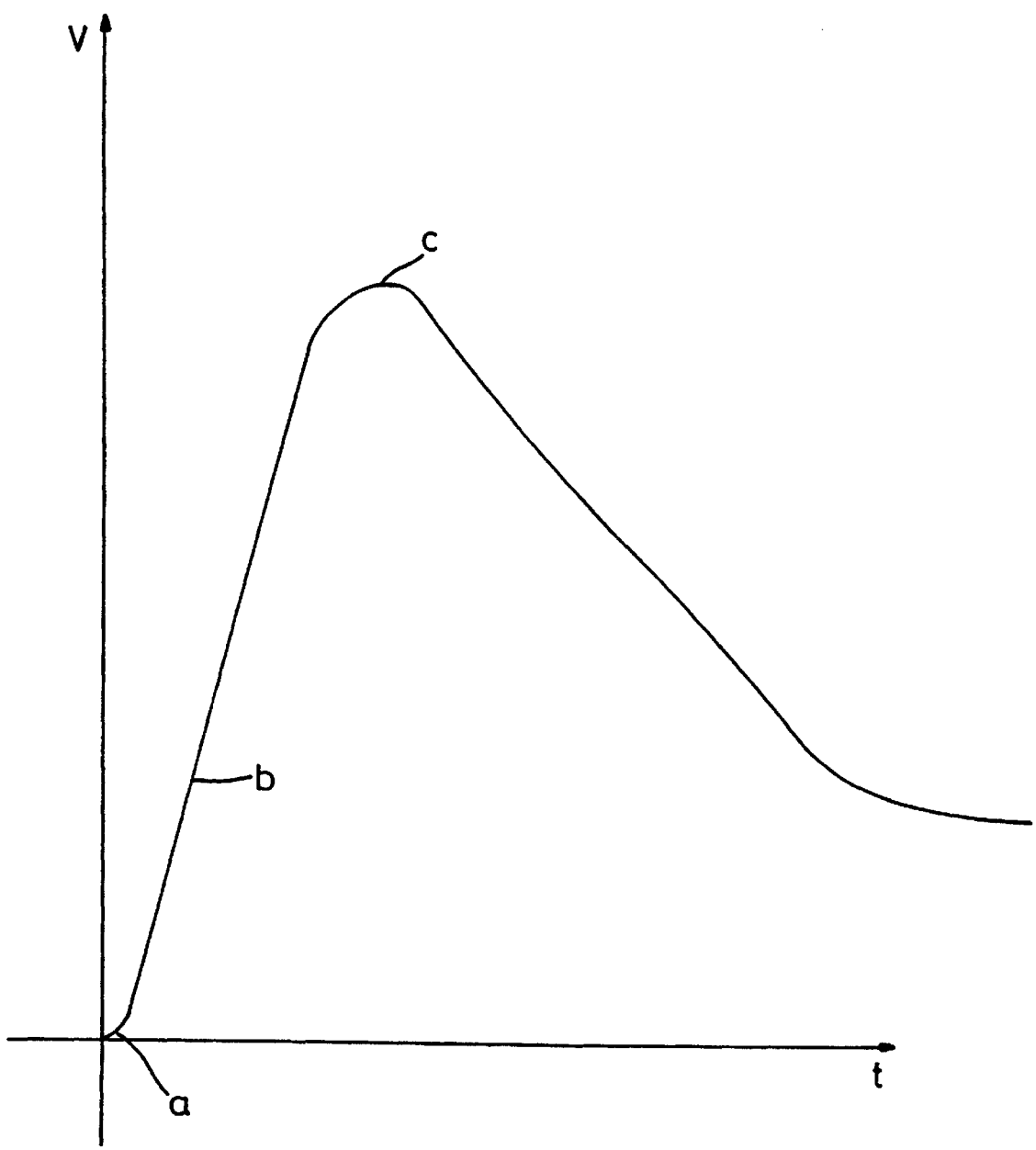
FIG. 1 is a diagram illustrating a typical fuel cell output.

The Applicant's investigations of fuel cells has determined that the initial gradient of a fuel cell response is linear and concentration dependent and therefore by measuring the initial gradient (i.e. the slope of the curve of the substantially linear or steady rate portion b of the cell output with respect to time as shown in FIG. 1), a fast reading may be obtained which is proportional to the alcohol concentration.

Figure 5:
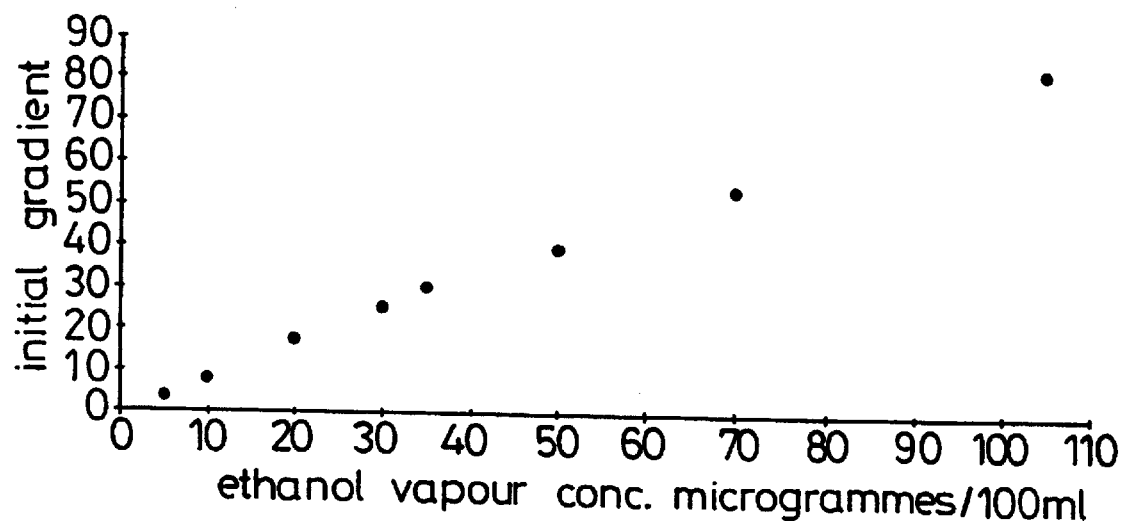
FIG. 5 is a graph indicating the relationship between initial gradient and ethanol vapour concentration for a particular fuel cell.

Thus as can be seen in Table 1 below a linear relationship between ethanol vapour concentration and initial gradient can be established. The results of Table 1 are represented graphically in the graph of FIG. 5.

TABLE 1

| Ethanol Vapour Concentration/$\mu$g 100 ml$^{-1}$ | Initial Gradient |
|---|---|
| 5 | 3.6 |
| 10 | 8.1 |
| 20 | 16.9 |
| 30 | 24.9 |
| 35 | 29.3 |
| 50 | 40.1 |
| 70 | 54.9 |
| 105 | 82.6 |

The measurements were taken using a LION (RTM) Alcolmeter SD-400 for successive samples of different concentrations at 20° C.–21° C. This piece of apparatus actually operates on a fixed volume. The temperature sensitivity of the initial gradient was also determined using a fixed 35 $\mu$g 100 ml$^{-1}$ ethanol standard and the results are shown in Table 2 below.

TABLE 2

| Temperature/° C. | Initial Gradient |
|---|---|
| −4 | 6.7 |
| 5 | 16.1 |
| 10 | 18.6 |
| 15 | 22.6 |
| 20 | 29.3 |
| 25 | 34.0 |
| 30 | 42.9 |
| 35 | 47.3 |
| 40 | 51.3 |

Figure 6:
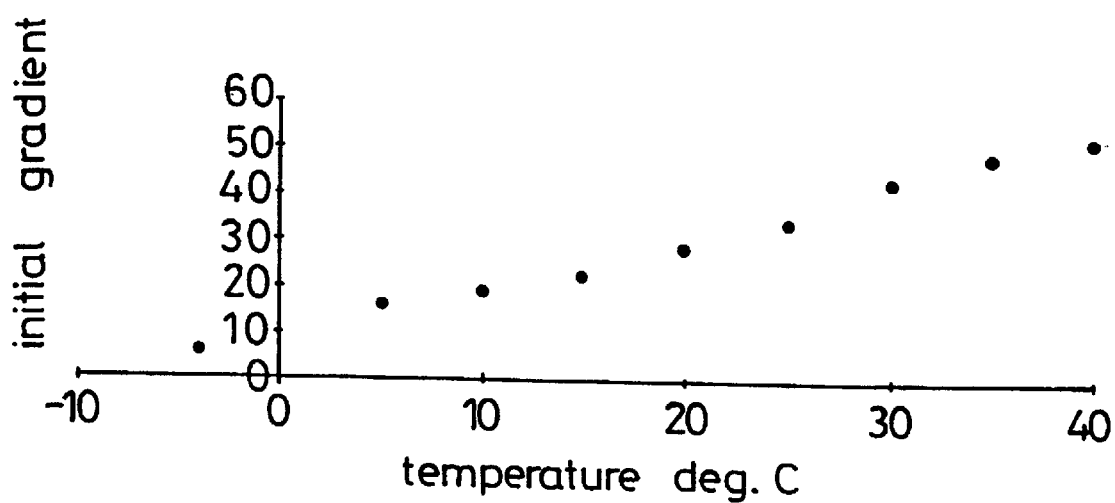
FIG. 6 indicates the relationship between initial gradient and temperature for that fuel cell.

The results from this table are plotted in FIG. 6 and again it will be seen that there is a relatively straight forward relationship. Thus such temperature variation can be overcome either by keeping the fuel cell at a constant temperature or by sensing the temperature and using a compensation algorithm or look-up tables.

The fuel cells were then subjected to a flow of vapour sample at one litre per minute and varying flushing times were used. Initial gradient was measured for several flush times (i.e. for several different volumes) and the results for a 20 $\mu$g 100 ml$^{-1}$ ethanol vapour standard are tabulated in Table 3 below.

TABLE 3

| Flushing Time/seconds | Initial Gradient |
|---|---|
| 4 | 274 |
| 5 | 277 |
| 6 | 277 |
| 7 | 276 |
| 8 | 277 |
| 9 | 277 |
| 10 | 276 |

These show that the initial gradient is not volume dependent. However changes in the flow rate did cause a variation in output until a PTFE membrane was used to cover the working electrode. Thereafter variations in the flow rate between 2–30 litres per minute produce no variation in the initial gradient.

Other techniques could be introduced to overcome flow rate sensitivity for example a breath tube having a constant flow rate mouth piece would overcome this difficulty.

Figure 2:
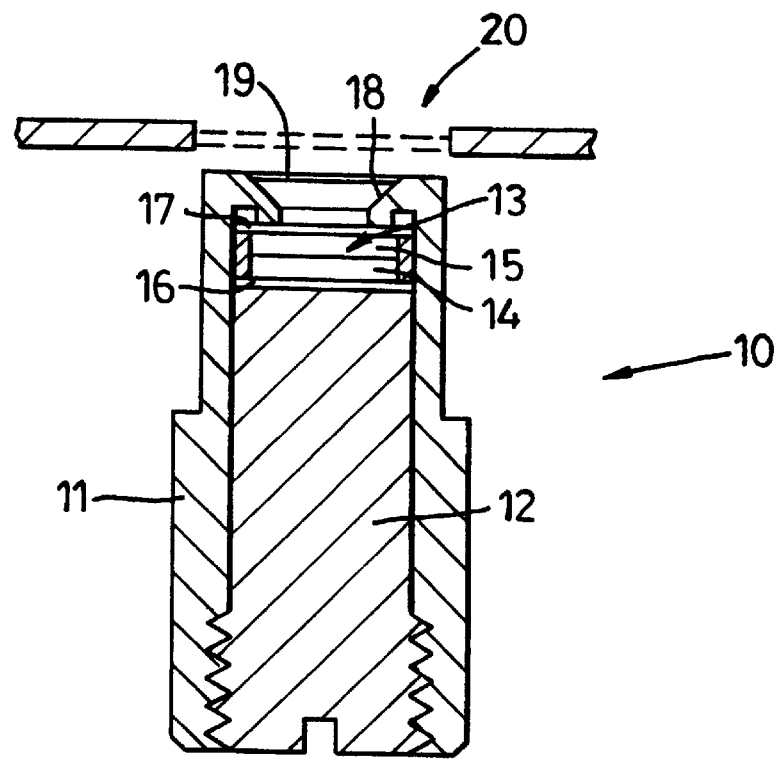
FIG. 2 is a cross-section of a fuel cell for use in the apparatus of the invention.

FIG. 2 illustrates at 10 a miniature fuel cell of the type which is particularly efficacious in this invention. The fuel cell 10 comprises a case 11; a fuel cell holder 12, which screws in the case 11; a fuel cell 13 comprising a counter electrode 14 and annular gold plated stainless steel contacts 16 and 17 which engage the electrodes 14 and 15 respectively. The electrodes 14 and 15 are fabricated from catalytic grade platinum black supported on a porous PVC matrix and conveniently have a diameter of 5 millimeters or less. The electrodes are thoroughly impregnated with aqueous sulphuric acid electrolyte prior to assembly.

The casing 11 defines a mouth 18, across which extends the hydrophobic gas permeable membrane 19, such as a PTFE membrane. Alternatively the membrane 19 may be mounted on the annular contact 17.

A shutter mechanism 20 is diagrammatically indicated overlying the mouth 18; this may be in the form of a camera style iris or a sliding plate. Alternatively other means may be used to present the sample to the mouth 18.

Figure 3:
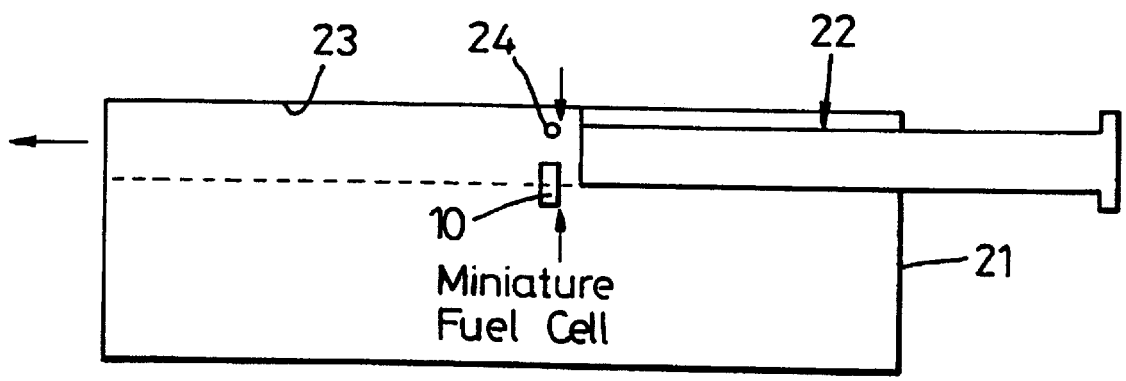
FIG. 3 is a schematic view of a breath alcohol tester incorporating the fuel cell of FIG. 2.

Breath testing apparatus is diagrammatically illustrated in FIG. 3 and comprises a body 21 into which is inserted a breath tube 22. The body 21 defines a sample part 23 as a continuation of the tube 21. The fuel cell 10 is mounted at right angles to the sample part 23 near the outlet of the breath tube 22. The cell can either simply be opened so that it takes a reading of the initial breath, or may be closed by the shutter arrangement 20, which can be controlled by conventional means for determining that sufficient air has been voided from the user's lungs to be testing alveolar breath. Most such systems comprise a combination of a pressure detector and a timer and they are well known in the art. One is diagrammatically illustrated at 24.

Figure 4:
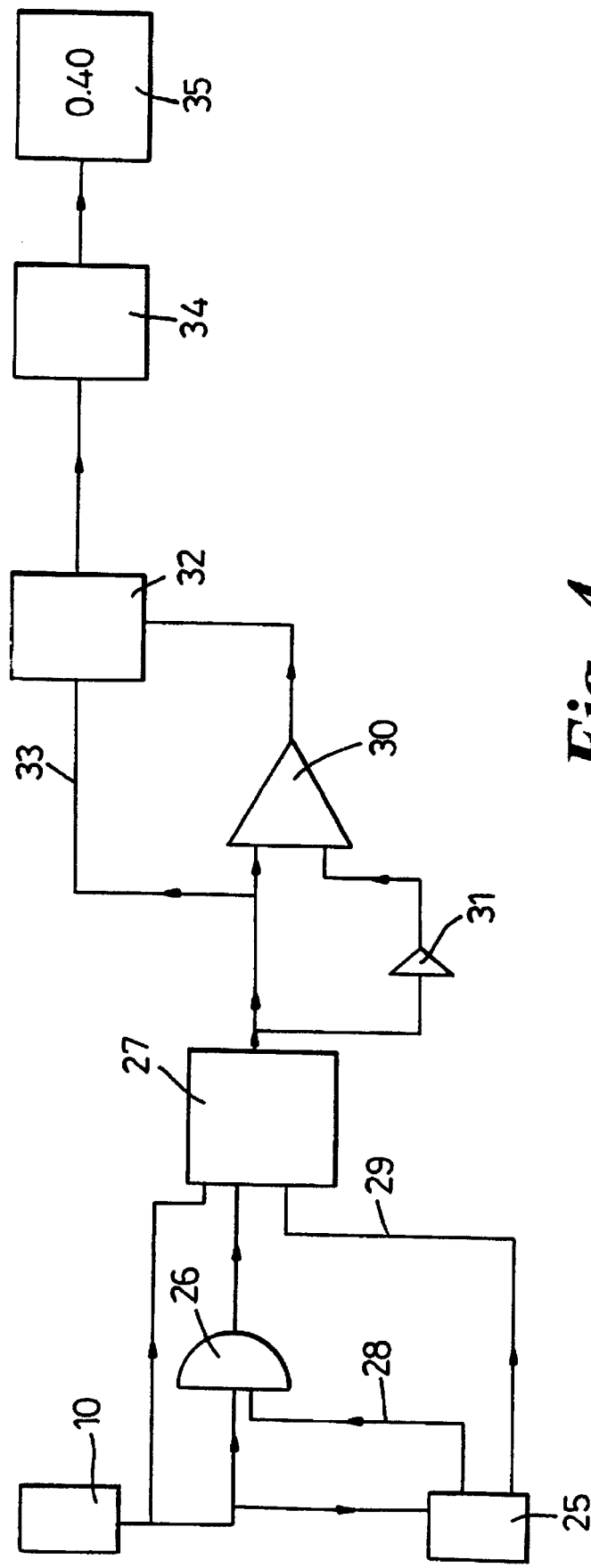
FIG. 4 is a schematic diagram of the circuit for producing a display of a vapour concentration.

FIG. 4 illustrates a processing circuit for the apparatus 21. Thus the output of the fuel cell 10 is fed simultaneously to a clock 25, an AND gate 26 and a gradient determining circuit 27. The output of the fuel cell 10 starts the clock 25 which produces its own output on line 28 after a short time period (corresponding to the life of the non-linear portion (a)) has expired. This output is fed to the AND gate 26, which on receiving it feeds a start signal to the circuit 27, which begins determining the gradient of the fuel cell output and continues to do so until it receives a stop signal from the clock 25 on line 29 or the clock stops. The output of the gradient determining circuit 27 is fed directly to one input of a comparator 30 and, via a delay 31, to the other input of the comparator 30. When the comparator identifies two successive gradient determinations which are equal it produces a gateing output, which is passed to gate 32. That in turn is receiving continuous gradient determinations on line 33 and, on receipt of the gateing pass, passes the current determination to a computational unit 34 that generates an ethanol vapour concentration signal from the determination gradient, for example in accordance with the graph of FIG. 5. The signal is then fed to display 35.

It will be appreciated that the principle of obtaining vapour concentration from the gradient of the straight line portion of the curve is generally applicable to fuel cells and is not linked to the configuration shown in the drawings.

What is claimed is:

1. A method of measuring ethanol vapour concentration comprising:

introducing a sample into a fuel cell to generate an output which is proportional to the vapour concentration, said output rising to a peak at a substantially steady rate after an initial non-linear portion, determining the gradient of the steady rate portion of the output with respect to time and, generating an ethanol vapour concentration signal from the determined gradient.

2. A method as claimed in claim 1 wherein the gradient is determined in a predetermined time window after the start of the output.

3. A method as claimed in claim 1 or claim 2 including:

comparing successive gradient determinations and selecting a gradient determination for generating the concentration after at least a pair of successive determinations are substantially equal.

4. Apparatus for measuring ethanol vapour concentration including:

a fuel cell for generating an output which is proportional to the concentration of the vapour to which it is exposed, said output rising to a peak at a substantially steady rate after an initial non-linear portion, means for determining the gradient of the steady rate portion of the output and, means for generating an ethanol vapour concentration signal from the determined gradient.

5. Apparatus as claimed in claim 4 further comprising a gas permeable membrane overlying the working electrode of the fuel cell.

6. Apparatus as claimed in claim 5 wherein the membrane is a PTFE membrane.

7. Apparatus as claimed in claim 4 having a body defining a sample path and further comprising means for exposing the fuel cell to vapour in the sample path.

8. Apparatus as claimed in claim 7 wherein the exposing means comprises means for changing the relative gas pressure adjacent the fuel cell.

9. Apparatus as claimed in claim 7 wherein the exposing means comprises a shutter.

\* \* \* \* \*